US009061970B2

(12) United States Patent
Mastroianni

(10) Patent No.: US 9,061,970 B2
(45) Date of Patent: Jun. 23, 2015

(54) PRODUCTION OF COMPOUNDS COMPRISING NITRILE FUNCTIONAL GROUPS

(75) Inventor: Sergio Mastroianni, Lyons (FR)

(73) Assignee: INVISTA North America S.a.r.l., Wilmington, DE (US)

(*) Notice: Subject to any disclaimer, the term of this patent is extended or adjusted under 35 U.S.C. 154(b) by 424 days.

(21) Appl. No.: 12/864,101

(22) PCT Filed: Jan. 12, 2009

(86) PCT No.: PCT/EP2009/050265
§ 371 (c)(1),
(2), (4) Date: Sep. 29, 2010

(87) PCT Pub. No.: WO2009/092639
PCT Pub. Date: Jul. 30, 2009

(65) Prior Publication Data
US 2011/0021804 A1    Jan. 27, 2011

(30) Foreign Application Priority Data
Jan. 25, 2008    (FR) ...................................... 08 00381

(51) Int. Cl.
C07C 253/10    (2006.01)
B01J 31/14    (2006.01)
B01J 31/18    (2006.01)
B01J 31/24    (2006.01)

(52) U.S. Cl.
CPC ............. *C07C 253/10* (2013.01); *B01J 31/143* (2013.01); *B01J 31/146* (2013.01); *B01J 31/185* (2013.01); *B01J 31/2409* (2013.01); *B01J 2231/32* (2013.01); *B01J 2531/847* (2013.01)

(58) Field of Classification Search
None
See application file for complete search history.

(56) References Cited

U.S. PATENT DOCUMENTS

| | | | |
|---|---|---|---|
| 3,496,215 A | 2/1970 | Drinkard, Jr. et al. | |
| 3,496,217 A | 2/1970 | Drinkard, Jr. et al. | |
| 3,496,218 A | 2/1970 | Drinkard, Jr. et al. | |
| 3,631,191 A | 12/1971 | Kane et al. | |
| 3,655,723 A | 4/1972 | Drinkard, Jr. | |
| 3,694,485 A | 9/1972 | Drinkard, Jr. et al. | |
| 3,766,231 A | 10/1973 | Gosser et al. | |
| 3,766,237 A | 10/1973 | Chia et al. | |
| 3,773,809 A | 11/1973 | Walter | |
| 3,864,380 A * | 2/1975 | King et al. | 558/338 |
| 4,082,811 A | 4/1978 | Shook, Jr. | |
| 4,339,395 A | 7/1982 | Barnette et al. | |
| 4,416,825 A | 11/1983 | Ostermaier | |
| 4,774,353 A | 9/1988 | Hall et al. | |
| 4,874,884 A * | 10/1989 | McKinney et al. | 558/338 |
| 5,512,696 A | 4/1996 | Kreutzer et al. | |
| 5,693,843 A | 12/1997 | Breikss et al. | |
| 5,847,191 A | 12/1998 | Bunel et al. | |
| 5,981,772 A | 11/1999 | Foo et al. | |
| 6,048,996 A | 4/2000 | Clarkson et al. | |
| 6,127,567 A | 10/2000 | Garner et al. | |
| 6,153,758 A | 11/2000 | Sannicolo et al. | |
| 6,521,778 B1 | 2/2003 | Fischer et al. | |
| 6,770,770 B1 | 8/2004 | Baumann et al. | |
| 7,084,293 B2 | 8/2006 | Rosier et al. | |
| 7,098,358 B2 | 8/2006 | Burattin et al. | |
| 7,105,696 B2 | 9/2006 | Burattin et al. | |
| 7,442,825 B2 | 10/2008 | Galland et al. | |
| 7,470,805 B2 | 12/2008 | Rosier et al. | |
| 7,485,741 B2 | 2/2009 | Bourgeois et al. | |
| 7,550,407 B2 | 6/2009 | Bartsch et al. | |
| 7,612,223 B2 | 11/2009 | Rosier et al. | |
| 7,777,068 B2 | 8/2010 | Bartsch et al. | |
| 2006/0258874 A1 * | 11/2006 | Bartsch et al. | 558/338 |

(Continued)

FOREIGN PATENT DOCUMENTS

DE    199 53 058 A1    5/2001
DE    10314761 A1    10/2004

(Continued)

OTHER PUBLICATIONS

Janusz Serwatowski et al., "New Tetrameric Alkylmetal Boryloxides [($\mu^3$-R$_2$BO)MR']$_4$ of Zinc and Cadmium with Heterocubane Structure," Inorg. Chem., 1999, pp. 4937-4941, vol. 38, No. 22.

Janusz Serwatowski et al., "Diverse Reactivity of Dialkylaluminum Dimesitylboryloxides [($\mu$-Mes$_2$BO)AIR$_2$]$_2$. Synthetic and Structural Study," Inorg. Chem. 2000, pp. 5763-5767, vol. 39, No. 25.

Vernon C. Gibson et al., "Formation and Unexpected Catalytic Reactivity of Oranoaluminum Boryloxides," Inorg. Chem., 2001, pp. 826-827, vol. 40, No. 5.

(Continued)

*Primary Examiner* — Yun Qian
(74) *Attorney, Agent, or Firm* — Robert B. Furr, Jr.; Jeffrey A. Freeman

(57)    ABSTRACT

Compounds containing at least one nitrile functional group are produced by hydrocyanation of an organic compound having at least one site of non-conjugated unsaturation, having from 2 to 20 carbon atoms, by reaction with hydrogen cyanide in the presence of a catalytic system containing a complex of nickel having the oxidation state of zero with at least one organophosphorus ligand selected from the group consisting of organophosphites, organophosphonites, organophosphinites and organosphosphines and a cocatalyst of the Lewis acid type of formula:

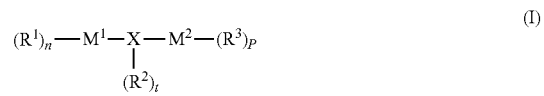

(I)

in which M1 and M2 are each elements selected from the group consisting of zinc, boron, aluminum, cadmium, gallium, indium and tin.

8 Claims, No Drawings

(56) References Cited

U.S. PATENT DOCUMENTS

| | | | |
|---|---|---|---|
| 2011/0021804 A1 | 1/2011 | Mastroianni | |
| 2011/0118499 A1* | 5/2011 | Mastroianni | 558/335 |
| 2011/0166376 A1* | 7/2011 | Mastroianni | 558/338 |
| 2011/0288327 A1* | 11/2011 | Mastroianni | 558/338 |

FOREIGN PATENT DOCUMENTS

| | | |
|---|---|---|
| EP | 0 336 314 A2 | 10/1989 |
| FR | 1 529 134 A1 | 5/1968 |
| FR | 2 069 411 A1 | 9/1971 |
| FR | 2 523 974 A1 | 9/1983 |
| FR | 2 830 530 A1 | 4/2003 |
| FR | 2 849 027 A1 | 6/2004 |
| FR | 2 854 892 A1 | 11/2004 |
| FR | 2 845 379 A1 | 4/2009 |
| WO | WO 96/22968 | 8/1996 |
| WO | WO 99/06355 A1 | 2/1999 |
| WO | WO 99/06356 A1 | 2/1999 |
| WO | WO 99/06357 A1 | 2/1999 |
| WO | WO 99/52632 A1 | 10/1999 |
| WO | WO 99/62855 A1 | 12/1999 |
| WO | WO 99/64155 A1 | 12/1999 |
| WO | WO 99/65506 A1 | 12/1999 |
| WO | WO 01/36429 A1 | 5/2001 |
| WO | WO 02/13964 A1 | 2/2002 |
| WO | WO 02/30854 A2 | 4/2002 |
| WO | WO 02/053527 A1 | 7/2002 |
| WO | WO 03/011457 A1 | 2/2003 |
| WO | WO 03/031392 A1 | 4/2003 |
| WO | WO 03/068729 A1 | 8/2003 |
| WO | WO 2004/007432 A1 | 1/2004 |
| WO | WO 2004/007434 A1 | 1/2004 |
| WO | WO 2004/060855 A1 | 7/2004 |
| WO | WO 2004/065352 A1 | 8/2004 |
| WO | WO 2004/087314 A1 | 10/2004 |
| WO | WO 2009/092639 A1 | 7/2009 |

OTHER PUBLICATIONS

Oishi (Silicon(IV) Lewis Acids, in Lewis Acids in Organic Syth., 2000, ch. 9, p. 355-393).
International Search Report dated Jan. 25, 2010 issued in PCT/EP2009/062896.
International Search Report (PCT/ISN210) issued on May 25, 2010, by European Patent Office as the International Searching Authority for International Application No. PCT/EP2010/050521.
International Search Report dated Dec. 23, 2009, issued in PCT/EP2009/056916.
International Search Report dated Jul. 30, 2009, issued in PCT/EP2009/050265.
Office Action mailed May 9, 2013, in U.S. Appl. No. 13/123,721.
Final Office Action mailed Nov. 14, 2013, in U.S. Appl. No. 13/123,721.
Office Action mailed Jun. 6, 2014, in U.S. Appl. No. 13/123,721.
Final Office Action mailed Nov. 17, 2014, in U.S. Appl. No. 13/123,721.
Office Action mailed Oct. 25, 2013, in U.S. Appl. No. 13/146,610.
Final Office Action mailed Jul. 17, 2014, in U.S. Appl. No. 13/146,610.
Office Action mailed May 16, 2013, in U.S. Appl. No. 12/999,336.
Final Office Action mailed Dec. 5, 2013, in U.S. Appl. No. 12/999,336.
Advisory Action mailed Jun. 9, 2014, in U.S. Appl. No. 12/999,336.
Office Action mailed Oct. 10, 2014, in U.S. Appl. No. 12/999,336.

* cited by examiner

PRODUCTION OF COMPOUNDS COMPRISING NITRILE FUNCTIONAL GROUPS

CROSS-REFERENCE TO PRIOR EARLIER APPLICATIONS

This application is a United States national phase of PCT/EP 2009/050265, filed Jan. 12, 2009 and designating the United States (published in the French language on Jul. 30, 2009, as WO 2009/092639 A1; the title and abstract were also published in English), which claims foreign priority under 35 U.S.C. §119 of FR 0800381, filed Jan. 25, 2008, each hereby expressly incorporated by reference in its entirety and each assigned to the assignee hereof.

The present invention relates to a process for producing compounds comprising at least one nitrile function by hydrocyanation of a compound comprising at least one non-conjugated unsaturation.

It relates more particularly to a production process implementing the reaction of hydrogen cyanide with an organic compound comprising a non-conjugated unsaturation in the presence of a catalytic system comprising nickel having the oxidation state of zero (hereinafter referred to as Ni(0)) with at least one organophosphorus ligand and a cocatalyst belonging to the Lewis acid family.

Such processes have been known for many years and are exploited industrially, in particular for the production of a major chemical intermediate, adiponitrile. This compound is in particular used in the production of hexamethylenediamine, which is an important monomer for the production of polyamides and also an intermediate in the synthesis of diisocyanate compounds.

Thus, the company DU PONT DE NEMOURS has developed and exploited a process for producing adiponitrile by double hydrocyanation of butadiene. This reaction is generally catalysed by a catalytic system comprising a complex of nickel(0) with organophosphorus ligands. This system also comprises a cocatalyst, in particular in the second hydrocyanation step, i.e. hydrocyanation of unsaturated compounds comprising a nitrile function, such as pentenenitriles to dinitrile compounds.

Many cocatalysts have been proposed in patents and are generally compounds belonging to the Lewis acid family. The role of this cocatalyst or promoter is to limit the production of by-products and therefore to promote the formation of linear dinitrile compounds compared with the formation of branched dinitriles.

Thus, many metal halides, such as zinc chloride, zinc bromide, stannous chloride or stannous bromide, have already been proposed, for example in U.S. Pat. No. 3,496,217. Zinc chloride is the preferred cocatalyst.

Organic boron compounds such as triphenyl boron or compounds comprising two boron atoms, as described in U.S. Pat. No. 3,864,380 and U.S. Pat. No. 3,496,218, or organic tin compounds as in U.S. Pat. No. 4,874,884, have also been proposed.

These cocatalysts have different properties and make it possible to obtain selectivities for different linear dinitriles such as adiponitrile. Some of these cocatalysts have drawbacks associated with the difficulty in extracting them from the reaction medium or with the possibility and ease of extracting the catalytic system or the nickel(0) ligand in the presence of this cocatalyst, in order to recycle it.

There still exists a need to find new cocatalysts for obtaining selectivities for linear dinitriles that are of acceptable levels and easy to use.

One of the aims of the present invention is to provide a new family of compatible cocatalysts which give adiponitrile-selectivity levels that are suitable in the pentenenitrile hydrocyanation reaction.

To this effect, the invention provides a process for producing compounds comprising at least one nitrile function by hydrocyanation of an organic compound comprising at least one non-conjugated unsaturation, comprising from 2 to 20 carbon atoms, by reaction with hydrogen cyanide in the presence of a catalytic system comprising a complex of nickel having the oxidation state of zero with at least one organophosphorus ligand chosen from the group comprising organophosphites, organophosphonites, organophosphinites and organophosphines and a cocatalyst, characterized in that the cocatalyst is an organometallic compound corresponding to general formula I:

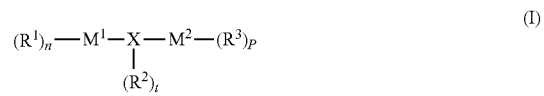

in which:

R$^1$, R$^2$ and R$^3$, which may be identical or different, represent a branched or unbranched, aliphatic organic radical, a substituted or unsubstituted, aromatic or cycloaliphatic radical, or a halogen atom, M$^1$, M$^2$, which may be identical or different, represent an element of valency m$^1$, m$^2$, respectively, chosen from the group comprising zinc, boron, aluminium, cadmium, gallium, indium and tin, it being impossible for M$^1$ and M$^2$ to simultaneously represent boron, X is an element of valency x chosen from the group comprising oxygen, carbon, nitrogen, silicon, sulphur and phosphorus, n is an integer equal to m$^1$−1, p is an integer equal to m$^2$−1, t is an integer equal to x−2.

According to one preferred embodiment, the elements M$^1$ and M$^2$ are chosen from the group comprising boron, aluminium and zinc.

Preferably, M$^2$ represents aluminium or zinc, and M$^1$ represents boron or aluminium. In an even more preferred embodiment, M$^2$ represents aluminium or zinc, M$^1$ represents boron or aluminium, and X represents oxygen.

According to another characteristic of the invention, the radicals R$^1$ and R$^3$ are linear or branched alkyl radicals containing from 1 to 6 carbon atoms, substituted or unsubstituted phenyl radicals, or halogen atoms, preferably chlorine.

The compounds that can be used as catalysts in the hydrocyanation processes are, for example:

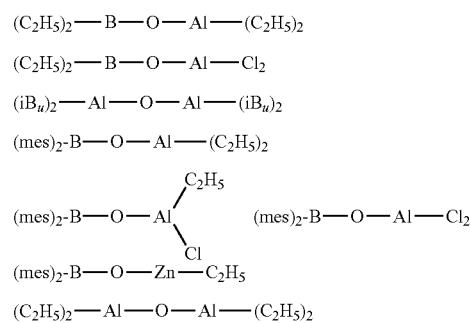

in which:

iBu represents the isobutyl radical, mes represents a mesityl(2,4,6-trimethylphenyl) group.

The compounds used as catalyst, in accordance with the invention, may be present in the form of independent molecules or in a form aggregated by noncovalent bonds such as dative bonds, thus forming dimers, trimers or tetramers.

By way of example, the compound $(mes)_2$-B—O—Al—$(C_2H_5)_2$ is generally present in the form of dimer $[(\mu\text{-mes})_2$-B—O—Al—$(C_2H_5)_2]_2$. In the interests of greater clarity, in the present text, reference will be made only to the simple molecule of each compound, without thereby limiting the scope of the patent to this simple form.

In one preferred embodiment of the invention, the catalytic system of the invention contains a cocatalyst in accordance with the invention in a molar ratio of cocatalyst relative to the number of nickel atoms of between 0.01 and 50, and preferably between 0.1 and 10.

The cocatalysts of the invention are compounds which are described in the literature, as is the process for producing them. By way of example, as articles describing the processes for producing these compounds, mention may be made of the articles by J. Serwatowski et al., published in Inorganic Chemistry, 1999, 38, 4937 and Inorganic Chemistry, 2000, 39, 5763, and also the article by V. G. Gibson et al., published in Inorganic Chemistry, 2001, 40, 826.

Examples of the production of these compounds are given below.

The catalytic system of the invention comprises a complex of nickel(0) with at least one organophosphorus compound, preferably a monodentate compound such as triphenylphosphite or tritolylphosphite, described for example in U.S. Pat. No. 3,496,215, DE19953058, FR1529134, FR2069411, U.S. Pat. No. 3,631,191, U.S. Pat. No. 3,766,231 or FR2523974, or a bidentate compound such as the organophosphite compounds described in Patents WO9906355, WO9906356, WO9906357, WO9906358, WO9952632, WO9965506, WO9962855, U.S. Pat. No. 5,693,843, WO961182, WO9622968, U.S. Pat. No. 5,981,772, WO0136429, WO9964155, WO0213964 and U.S. Pat. No. 6,127,567.

It is also possible to use complexes of nickel(0) with monodentate or bidentate organophosphine compounds as described in Patents WO02/30854, WO02/053527, WO03/068729, WO04/007435, WO04/007432, FR2845379 and WO2004/060855, and more particularly the DPPX described in Patent WO2003/031392.

Similarly, the catalytic system of the invention may comprise a complex of nickel(0) with monodentate or bidentate organophosphorus compounds belonging to the organophosphonite or organophosphinite family.

It is also possible to use the cocatalysts of the invention with a nickel(0) complex obtained with a mixture of organophosphite monodentate ligand and of bidentate ligand chosen from the families of compounds belonging to the organophosphites, organophosphonites, organophosphinites or organophosphines, as described in Patents WO03/011457 and WO2004/065352.

The description of the hydrocyanation process is given in several patents, including those mentioned above, and also in the articles by C. A. Tolman published in the reviews Organometallics 3 (1984) 33 et seq., Advances in Catalysis (1985) 33-1; J. Chem. Soc. Chem. Commun (1991)-1292 and (1991)-803.

Briefly, the process for producing compounds comprising at least one nitrile function, and more particularly dinitrile compounds such as adiponitrile, consists in reacting, in a first step, a diolefin such as 1,3-butadiene with hydrogen cyanide, generally in the absence of solvent and in the presence of a catalytic system. The reaction is carried out under pressure so as to be in a liquid medium. The unsaturated nitrile compounds are separated by successive distillations. The linear nitrile compounds, such as pentenenitriles, are fed into a second hydrocyanation step.

Advantageously, the nonlinear unsaturated nitriles obtained in the first step are subjected to an isomerization step in order to convert them to linear unsaturated nitriles, which are also introduced into the second hydrocyanation step.

In the second hydrocyanation step, the linear unsaturated nitriles are reacted with hydrogen cyanide in the presence of a catalytic system.

The dinitrile compounds formed are separated by successive distillations after extraction of the catalytic system from the reaction medium. Several processes for extracting the catalytic system are described, for example, in U.S. Pat. Nos. 3,773,809, 4,082,811, 4,339,395 and 5,847,191. Generally, the catalytic system can be separated from the reaction medium by separation into two phases by settling out, obtained by control of the ratios between the mononitrile compounds and the dinitrile compounds contained in the medium. This separation can be improved by the addition of ammonia. It is also possible to precipitate the catalytic system in order to recover it and recycle it, or to use a nonpolar solvent for extracting the catalytic system and separating it from the nitrile products.

The temperature conditions for these various steps are between 10 and 200° C.

The catalytic systems used in the first and second hydrocyanation steps and also in the isomerization step are generally similar, i.e. they contain an identical nickel(0) complex. However, the ratio between the number of nickel atoms and the number of ligand molecules may be different in each of these steps, and also the concentration of the catalytic system in the medium.

Preferably, the cocatalyst is present only in the catalytic system used for the second hydrocyanation step. However, it may also be present in the isomerization step.

The characteristics and performance levels of the process and therefore of the catalytic system used are determined and illustrated by the degree of conversion (DC) of the compound introduced, in particular of the unsaturated mononitrile introduced in the second step, and by the linearity with respect to linear dinitriles produced, i.e. the number of moles of linear dinitriles relative to the number of moles of dinitriles formed. In the case of the production of adiponitrile, the linearity corresponds to the percentage of moles of adiponitrile (AdN) obtained relative to the numbers of moles of dinitriles formed (AdN+ESN+MGN).

The invention will be illustrated more clearly by means of the examples given below, only by way of indication, relating to the production of adiponitrile by hydrocyanation of 3-pentenenitrile. In these examples, the 3-pentenenitrile is a commercially available compound.

In these examples, the following abbreviations are used:

Cod: cyclooctadiene
3PN: 3-pentenenitrile
AdN: adiponitrile
ESN: ethylsuccinonitrile
MGN: methylglutaronitrile
TTP: tri-para-tolylphosphite
TEA: triethylaluminium
DEAC: diethylaluminium chloride EADC: ethylaluminium dichloride
TiBAO: tetraisobutyldialuminoxane
mes: mesityl(2,4,6-trimethylphenyl) group
Et: ethyl group
iBu: isobutyl group
Ph: phenyl group
DPPX: bis(diphenylphosphinomethyl)-1,2-benzene
DC(Y): degree of conversion of the product to be hydrocyanated Y, corresponding to the ratio of the number of converted moles of Y to the number of initial moles of Y
linearity (L): ratio of the number of moles of AdN formed to the number of moles of dinitriles formed (sum of the moles of AdN, ESN and MGN)
Synthesis of the Cocatalyst Compounds of Formula I The syntheses of the various compounds were carried out according to the processes described in the articles published in the review Inorganic Chemistry mentioned above. These syntheses are carried out under an argon atmosphere.

EXAMPLE 1

Synthesis of $(mes)_2$-B—O—Al—$(C_2H_5)_2$ 179 mg of a molar solution of TEA in hexane are added rapidly and with stirring to a solution of dimesitylborinic acid (68 mg) in anhydrous toluene (1 ml). The mixture is kept stirring and at temperature for 30 minutes before being completely used as catalyst in the hydrocyanation test.

EXAMPLE 2

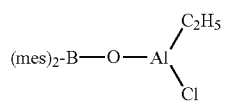

175 mg of a molar solution of DEAC in hexane are added rapidly and with stirring to a solution of dimesitylborinic acid (66 mg) in anhydrous toluene (1 ml). The mixture is kept stirring and at temperature for 30 minutes before being completely used for the hydrocyanation test.

EXAMPLE 3

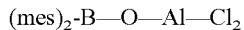

182 mg of a molar solution of EADC in hexane are added rapidly and with stirring to a solution of dimesitylborinic acid (68 mg) in anhydrous toluene (1 ml). The mixture is kept stirring and at temperature for 30 minutes before being completely used for the hydrocyanation test.

EXAMPLE 4

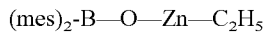

221 mg of a 1.1 molar solution of $ZnEt_2$ in toluene are added rapidly and with stirring to a solution of dimesitylborinic acid (67 mg) in anhydrous toluene (1 ml). The mixture is kept stirring and at temperature for 30 minutes before being completely used for the hydrocyanation test.

EXAMPLES

Hydrocyanation of 3-PN so as to Give AdN

The procedure is the following:

The following are loaded successively, under an argon atmosphere, into a 60 ml glass tube of Schott type, equipped with a septum stopper:

the ligand [5 molar equivalents of ligand per atom of Ni if the ligand is a monodentate such as TTP, or 2.5 molar equivalents of ligand per atom of Ni if the ligand is bidentate, such as DPPX], 1.21 g (15 mmol, 30 equivalents) of anhydrous 3PN, 138 mg (0.5 mmol, 1 equivalent) of $Ni(Cod)_2$, Lewis acid (see the indications in Tables I and II below for the nature and the amount).

The mixture is brought to 70° C. with stirring. Acetone cyanohydrin, an HCN generator, is injected into the reaction medium via a syringe driver with a flow rate of 0.45 ml per hour. After injecting for 3 hours, the syringe driver is stopped. The mixture is cooled to ambient temperature, diluted with acetone and analysed by gas chromatography.

The results are given in Tables I and II below.

TABLE I

Comparative Examples 5 to 7

| Example | Ligand | Lewis acid | Lewis acid/Ni | DC (3PN) | Linearity |
|---|---|---|---|---|---|
| 5 | TTP | $(mes)_2BOH$ | 1 | 23.6 | 67.7 |
| 6 | DPPX | ZnCl2 | 1 | 72.8 | 59.0 |
| 7 | TTP | $Ph_2BOBPh_2$ | 0.5 | 14.3 | 73.8 |

TABLE 2

Examples 8 to 16

| Example | Ligand | Lewis acid | Lewis acid/Ni | DC (3PN) | Linearity |
|---|---|---|---|---|---|
| 8 | TTP | TiBAO | 0.5 | 47.9 | 76.8 |
| 9 | TTP | TiBAO | 0.25 | 36.7 | 78.7 |
| 10 | TTP | Ex. 1 | 0.5 | 38.2 | 76.2 |
| 11 | TTP | Ex. 2 | 0.5 | 34.0 | 73.5 |
| 12 | TTP | Ex. 3 | 0.5 | 35.8 | 71.1 |
| 13 | TTP | Ex. 4 | 0.5 | 51 | 78.2 |
| 14 | DPPX | TiBAO | 0.5 | 78.4 | 84.7 |
| 15 | DPPX | TiBAO | 0.25 | 77.8 | 86.4 |
| 16 | DPPX | Ex. 4 | 0.5 | 33.3 | 84.1 |

The invention claimed is:

1. A process for the preparation of a compound containing at least one nitrile functional group, comprising the hydrocyanation of an organic compound having at least one site of non-conjugated unsaturation, having from 5 to 20 carbon atoms, by reaction with hydrogen cyanide in the presence of a catalytic system which comprises a complex of nickel having the oxidation state of zero with at least one organophosphorus ligand selected from the group consisting of organophosphites, organophosphonites, organophosphinites and organophosphines and a cocatalyst, wherein the cocatalyst is an organometallic compound corresponding to general formula (I):

$$(R^1)_n-M^1-X-M^2-(R^3)_p \quad (I)$$

in which:
  $R^1$ and $R^3$, which are identical or different, are each a branched or unbranched, aliphatic organic radical, a substituted or unsubstituted, aromatic or cycloaliphatic radical, or a halogen atom,
  $M^1$, $M^2$, which are identical or different, are each an element of valency $m^1$, $m^2$, respectively, selected from the group consisting of zinc, boron, aluminum, cadmium, gallium, indium and tin, with the proviso that $M^1$ and $M^2$ cannot simultaneously each be boron,
  X is oxygen,
  n is an integer equal to $m^1-1$, and
  p is an integer equal to $m^2-1$.

2. The process as defined by claim 1, wherein $M^2$ is aluminum or zinc, and $M^1$ is boron or aluminum.

3. The process as defined by claim 1, wherein the radicals $R^1$ and $R^3$ are each an alkyl radical having from 1 to 6 carbon atoms, a substituted or unsubstituted phenyl radical, or a halogen atom.

4. The process as defined by claim 1, wherein the cocatalyst is selected from the group consisting of the following compounds or dimers, trimers or tetramers thereof:

$$(C_2H_5)_2-B-O-Al-(C_2H_5)_2$$

$$(C_2H_5)_2-B-O-Al-Cl_2$$

$$(iBu)_2-Al-O-Al-(iBu)_2$$

$$(mes)_2\text{-}B-O-Al-(C_2H_5)_2$$

$$(mes)_2\text{-}B-O-Al\begin{smallmatrix}C_2H_5\\ \\Cl\end{smallmatrix} \qquad (mes)_2\text{-}B-O-Al-Cl_2$$

$$(mes)_2\text{-}B-O-Zn-C_2H_5$$

$$(C_2H_5)_2-Al-O-Al-(C_2H_5)_2$$

in which:
  iBu is the isobutyl radical, and
  mes is the mesityl(2,4,6-trimethylphenyl) group.

5. The process as defined by claim 1, wherein the catalytic system comprises a molar ratio of cocatalyst relative to the moles of Ni ranging from 0.1 to 10.

6. The process as defined by claim 1, wherein the organophosphorus ligand is selected from the group consisting of monodentate and bidentate organophosphorus compounds.

7. The process as defined by claim 1, wherein the organic compound is converted into dinitrile compounds and comprises pentenenitrile compounds.

8. The process as defined by claim 7, wherein the organic compound containing at least one nitrile functional group is adiponitrile.

\* \* \* \* \*